United States Patent [19]

Vaughn et al.

[11] Patent Number: 5,129,951
[45] Date of Patent: Jul. 14, 1992

[54] AROMATIC ALDEHYDES AND ALCOHOLS AS POTATO TUBER SPROUT INHIBITORS

[75] Inventors: Steven F. Vaughn, Peoria; Gayland F. Spencer, Metamora, both of Ill.

[73] Assignee: The United States of America as represented by the Secretary of Agriculture, Washington, D.C.

[21] Appl. No.: 723,118

[22] Filed: Jun. 28, 1991

[51] Int. Cl.$^5$ .................... A01N 31/08; A01N 35/04
[52] U.S. Cl. ........................................... 71/122; 71/77; 71/123
[58] Field of Search ...................... 71/122, 123, 77

[56] References Cited

U.S. PATENT DOCUMENTS 3,917,477 11/1975 Hashimoto et al. .................... 71/76

OTHER PUBLICATIONS

MacMillan, J. *Hormonal Regulation of Development I: Molecular Aspects of Plant Hormones,* Berlin: Springer-Verlag, 1980, p. 73.

M. V. Rama and P. Narasimham, "Comparative Efficacies of Chemical Sprout Inhibitors and Vapour Heat Treatments on the Control of Sprouting in STored Potatoes," J. Food Sci. Technol. 24: 40–42 (Jan./Feb. 1987).

T. J. Aliaga & W. Feldheim, "Inhibition of Sprouting of Stored Potatoes by the Essential Oil of the Muna Plant from South America," [transl. by G. E. Spencer], Ernahrung/Nutrition 9(4): 254–256 (1985) (in German).

W. Feldheim, "Practicability and Mode of Action of Quality Storage of Potatoes after Harvest," ]English translation] Report of lectures given at German Inst. for Quality Research (Plant Nutrition) (Mar. 1985).

T. Reymonds, "Comparative Effects of Alicyclic Compounds and Quinones on Inhibition of Lettuce Fruit Germination," Annals of Botany 60, 215–223 (1987).

R. G. Powell & G. F. Spencer, "Phytochemical Inhibitors of Velvetleaf (*Abutilon theophrasti*) Germination as Models for New Biorational Herbicides," *In* ACS Symp. Ser. No. 380: 211–232 (chap. 14) (1988).

H. Hitokoto et al., "Inhibitory Effects of Spices on Growth and Toxin Production of Toxigenic Fungi," Appl. Environ. Microbiol. 39: 818–822 (Apr. 1980).

R. S. Farag et al., "Influence of Some Spice Essential Oils on *Aspergillus parasiticus* Growth and Production of Aflatoxins in a Synthetic Medium," J. Food Sci. 54(1): 74–76 (1989).

A. Pauli & K. Knobloch, "Inhibitory Effects of Essential Oil Components on Growth of Food-Contaminating Fungi," Z. Lebensm. Unters. Forsch 185: 10–13 (1987).

N. Kurita et al., "Antifungal Activity of Components of Essential Oils," Agric. Biol. Chem. 45: 945–952 (1981).

Putnam and Tang (ed.), The Science of Allelopathy, John Wiley & Sons, New York, 1986, pp. 1–19, 64–65, 138–141, 171–188, 271–286.

Klingman and Ashton, Weed Science: Principles and Practices, Second edit., John Wiley & sons, New York, 1982, pp. 70–79.

Mazza and Pietrzak, "Headspace Volatiles and Sensory Characteristics of Earthy, Musty Flavoured Potatoes", Food Chemistry, 36: 97–112 (1990).

Coleman et al., "Isolation and Identification of Volatile Compounds from Baked Potatoes", J. Agric. Food Chem., 29: 42–48 (1981).

*Primary Examiner*—Carolyn Elmore
*Assistant Examiner*—S. Mark Clardy
*Attorney, Agent, or Firm*—M. Howard Silverstein; Randall E. Deck; John D. Fado

[57] ABSTRACT

A method for inhibiting sprouting of tubers including the step of exposing tubers to the aromatic aldehydes or alcohols: benzaldehyde, salicylaldehyde, cinnamaldehyde, hydrocinnamaldehyde, cuminaldehyde, thymol, or mixtures thereof.

27 Claims, No Drawings

AROMATIC ALDEHYDES AND ALCOHOLS AS POTATO TUBER SPROUT INHIBITORS

BACKGROUND OF THE INVENTION

1. Field of the Invention

The invention relates to a method for inhibiting potato tuber sprouting.

2. Description of the Prior Art

Typically, tubers are harvested, allowed to suberize (i.e., allow the "skin" or periderm layer to toughen) at warm temperatures for about 10 days, then gradually cooled down to the storage temperature of about 10° C. For the first 1-2 months after harvest, the tubers remain dormant and exhibit little inclination to sprout. However, after this period the tubers must be chemically treated to prevent sprouting from occurring, which sprouting causes numerous deleterious effects to the tubers. These include a loss of fresh weight, the conversion of starch to sugars, and a decrease in the quality and appearance of tubers sold fresh. Sprouts and the surrounding tissue also contain elevated levels of toxic glycoalkaloids, which are not destroyed by cooking.

Chlorpropham (CIPC; 1-methylethyl-3-chlorophenylcarbamate) is currently used to control sprouting throughout the industry. Although CIPC has been used effectively for over three decades, questions concerning its toxicology have been raised, and it is currently under review by the Environmental Protection Agency. CIPC is known to be among the three pesticides found in the highest concentrations in the diet of the average American [Gartrell et al., *J. Assoc. Off. Anal. Chem.*, 69:146-159 (1986)] and comprises over 90% of the total synthetic residues found in U.S. potatoes [Klocke et al., *J. Chem. Ecol.*, 13:2131-2141 (1987)]. Therefore, a pressing needs exists to find other, more environmentally acceptable sprout inhibitors for tubers.

Currently, several research groups in the United States and Europe are investigating alternative chemical inhibitors [Rama and Narasimham, *J Food Sci Technol.*, 24:40-42 (1987)].

For many centuries, the Incas of South America and their descendants have buried potato tubers in pits that are layered with soil and the leaves of Muna plants that belong to the mint family Lamiaceae, and the genera Minthostachys and Satureja. This treatment prevents sprouting and excessive fresh weight loss, and repels insect pests. These Muna plants contain copious amounts of essential oils that are substantially comprised of monoterpenes. Aliaga and Feldheim [*Ernahrung*, 9:254-256 (1985)] and Feldheim ["Practicability and Mode of Action of Quality Storage of Potatoes After Harvest," In Report of a Lecture Given to the German Institute for Quality Research (Plant Nutrition Products), March 1985, 6 pages] reported that the oil from the Muna plants was more effective than CIPC in inhibiting sprouting, fresh weight loss, and the incidence of rotted tuber parts over a period of 120 days. The authors also reported that the main components of the oil, including the monoterpenes α- and β-pinene and limonene, and the oxygenated monoterpenes pulegone and menthone/isomenthone, are effective in this regard.

Various aromatic acids, aldehydes, phenols and their derivatives are known to be phytotoxic [Putnam and Tang, "Allelopathy: State of the Science," in Putnam and Tang (ed.), The Science of Allelopathy, John Wiley & Sons, N.Y., 1986, pages 1-19]. In particular, cinnamic and benzoic acid derivatives have been frequently reported as being involved in allelopathy among plants [Putnam and Tang, ibid.]. These compounds are derived from the amino acids phenylalanine and tyrosine via the shikimic acid pathway and may be released from plant residues at phytotoxic levels [Mandava, "Chemistry and Biology of Allelopathic Agents," in Thompson (ed.), The Chemistry of Allelopathy, American Chemical Society, Washington, D.C., 1985, pages 33-54].

Volatile aromatic compounds are commonly present in plant essential oils, and many of these are used in substantial quantities as flavorings and in perfumes [Leung, in Encyclopedia of Common Natural Ingredients Used in Foods, Drugs, and Cosmetics, Johny Wiley & Sons, N.Y., 1980, page 409]. Benzaldehyde, salicylaldehyde and substituted benzoic acids have been found in uncooked and baked potato tubers [Coleman et al., *J. Agric. Food Chem.*, 29:42-49 (1981); Mazza and Pietrzak, *Food Chem.*, 36:97-112 (1990); and Nursten and Sheen, *J. Sci. Food Agric.*, 25:643-663 (1974)]. Several of these compounds have been shown to be inhibitory to the growth of plants, fungi, and bacteria [Farag et al., *J. Food Sci.*, 54:74-76 (1980); Hitokoto et al., *Appl. Environ. Microbiol.*, 39:818-822 (1980); Kurita et al., *Agric. Biol. Chem.*, 45:945-952 (1981); Pauli and Knobloch, *Z. Lebensm. Unters. Forsch.*, 185:10-13 (1987); Powell and Spencer, "Phytochemical Inhibitors of Velvetleaf (*Abutilon threoprasti*) Germination as Models for New Biorational Herbicides," in Cutler (ed.), Biologically Active Natural Products: Potential Use in Agriculture, ACS Symposium Series No. 380, American Chemical Society, Washington, D.C. (1988), pages 211-232; and Putnam and Tang, ibid.].

SUMMARY OF THE INVENTION

We have now surprisingly found that several aromatic aldehydes and alcohols, including thymol, hydrocinnamaldehyde and cuminaldehyde, and especially salicylaldehyde, cinnamaldehyde, and benzaldehyde, may be advantageous used to inhibit tuber sprouting, fresh weight loss, rotting, and fungal growth, by exposure of the tubers thereto. These aromatic aldehydes and alcohols exhibit substantially greater effectiveness and/or applicability than the compounds described in the prior art.

In accordance with this discovery, it is an object of this invention to provide an improved method for inhibiting tuber sprouting without necrosis or softening of the tuber. It is a further object to provide a method for inhibiting the sprouting of tubers under storage using aromatic aldehydes and alcohols applied as volatiles or as sprays.

Another object of this invention is to provide a method for inhibiting tuber sprouting using a compound that has low mammalian toxicity, is rapidly biodegradable, is inexpensive, and which does not impart an unpleasant taste or odor to the treated tubers.

Yet another object of the invention is to provide a method for inhibiting tuber sprouting which also prevents or controls fungal growth upon the tubers, thereby reducing postharvest decay losses.

These and other objects of the invention will become obvious from the ensuing description.

DETAILED DESCRIPTION OF THE INVENTION

The commercial importance of inhibiting sprouting and weight loss of tubers is well known. A need exists for an effective method to inhibit tuber sprouting which uses a compound that is environmentally acceptable, has low mammalian toxicity, and that does not result in necrosis or softening of the tubers, or impart an unpleasant taste or odor thereto.

According to this invention, there is provided a method for inhibiting sprouting of tubers including the step of exposing tubers to the aromatic aldehydes or alcohols: salicylaldehyde, cinnamaldehyde, benzaldehyde, thymol, hydrocinnamaldehyde (3-phenyl-propanal), cuminaldehyde or mixtures thereof. Exposure of the tubers to salicylaldehyde, cinnamaldehyde or benzaldehyde is particularly preferred. These aldehydes and alcohols may be applied alone in pure or substantially pure form, or optionally in a composition.

Suitable compositions of the aromatic aldehydes or alcohols of the invention may be prepared or may be naturally occurring. Naturally occurring compositions include but are not limited to oils or oleaginous materials such as cinnamon oils (containing cinnamaldehyde). Particularly preferred oils are those containing 1% or more, preferably 5% or more, by weight of the above-mentioned aldehydes or alcohols. The aldehydes or alcohols may also be formulated with an inert carrier or solvent. While as a practical matter, it is expected that pure or substantially pure aldehyde or alcohol will be formulated with a carrier, impure aldehydes or alcohols or an above-mentioned oil may be formulated with a carrier. The practitioner skilled in the art will recognize that the alcohol or aldehyde composition may be further formulated with, for example, emulsifying agents, other fungicides, or insecticides.

The process of the invention is effective for the inhibition of sprouting of a variety of tubers including but not limited to potatoes.

Preferred methods of exposure of the tubers to the aromatic alcohols or aldehydes involve exposure to the subject compounds while in a vapor phase. These methods take advantage of the relatively high volatility of these compounds, and enjoy the benefit of ease of application over a large volume of tubers. In this embodiment, exposure of the tubers to the compounds may be achieved by providing the compounds in liquid or solid form and allowing or causing the same to volatilize into the atmosphere adjacent to or surrounding the tubers. Without being limited thereto, especially favored techniques for enhancing this volatilization include fogging or fuming (e.g., heating), and/or simply passing air or some other inert gas over the compounds. Rather than initially providing the compounds in liquid or solid form, they may also be provided as a gas directly admitted into the atmosphere adjacent the tubers.

Alternatively, the aromatic aldehydes and alcohols may be applied directly onto the tubers while the liquid form, such as by dipping or spraying with a solution or emulsion thereof. For example, spraying the tubers with an emulsion of the aromatic aldehydes or alcohols as the tubers are passed along a conveyor into holding bins would provide a convenient mode of application. The practitioner skilled in the art will recognize that suitable formulations of the aromatic aldehydes or alcohols may optionally include a variety of well known solvents or suspending agents, including, but not limited to water. It is also understood that emulsifying agents may also be used.

In yet another alternative, the compounds may be incorporated into a slow release vehicle or carrier, such as by encapsulation or placement in a closed permeable container, to provide a controlled rate of release of the volatiles into the atmosphere over an extended period of time.

Exposure of the tubers to the composition may be initiated at any time after harvest or during the storage of the tubers. However, when the tubers are held in bins under normal storage conditions prevalent in the industry (about 10° C.), exposure preferably begins about 1-3 months after harvest or at such time that the tubers begin to sprout. Although the tubers may be continuously or intermittently exposed to the aldehydes and alcohols throughout storage, in the preferred embodiment, the tubers are only exposed to the subject compounds in a single occurrence. Throughout the period of exposure, the tubers will exhibit resistance to sprouting. Following removal of the tubers from exposure, resistance to sprouting may diminish, with the tubers beginning to sprout normally in a few days, or it may be prolonged. The duration of this resistance will vary with the specific aldehyde or alcohol used, its concentration, and the length of exposure. Surprisingly, it has been found that tubers exposed over relatively longer periods of time and/or at higher concentrations of the subject compounds, may resist sprouting indefinitely when removed from exposure thereto.

The absolute amount of the aromatic aldehydes or alcohols of the invention (salicylaldehyde, cinnamaldehyde, benzaldehyde, thymol, hydrocinnamaldehyde, and/or cuminaldehyde) and their concentration in a vapor phase or liquid composition may vary and are selected to provide an effective inhibition of tuber sprouting. An effective amount is defined herein as that quantity of the aromatic aldehydes or alchols that significantly inhibit tuber sprouting in comparison with untreated tubers. Especially preferred effective amounts include but are not limited to those quantities of the aromatic aldehydes or alcohols providing approximately complete inhibition of tuber sprouting (less than about 1% of eyes sprouting during treatment with the compounds). Suitable amounts and concentrations may be readily determined by the practitioner skilled in the art. The actual effective amount of the aromatic aldehydes and alcohols may vary with the specific compound used, the mode of application, the length of exposure to the compounds, the volume of tubers to be treated, environmental conditions such as temperature, humidity and air flow (affecting volatility and tuber metabolic activity), and the vehicle or carrier employed (affecting the release rate of the compounds into the atmosphere). As mentioned hereinabove, the amount may also vary in accordance with the duration of the resistance of the tubers to sprouting following exposure that is desired.

Without being limited thereto, preferred concentrations of the aromatic aldehydes or alcohols when directly applied on the tubers as a liquid may vary between about 0.1 and 100% by volume, especially between about 1 and 10%. When applied as volatiles, suitable ranges of vapor phase concentrations could be determined empirically. Although concentrations of the subject compounds are difficult to measure by gas chromatography, the practitioner skilled in the art will recognize that concentrations may be calculated by volatilizing known amounts of the compounds in a sealed container of predetermined volume, in which the tubers are placed.

EXAMPLE 1

The object of this first example was to screen aromatic aldehydes and alcohols for sprout inhibition as volatiles and would thus warrant further examination. Several physiochemical properties of these compounds, arranged in order from most to least volatile, are shown in Table I.

Untreated tubers of Solanum tuberosum L. cv 'Norchip' were stored at 4° C. for 3-5 months after harvest until used in tests.

TABLE I

Physiochemical Properties of Aromatic Compounds

| Compound | Chemical Function | Boiling Point (°C.) | Temperature (°C.) at Which Vapor Pressure Equals 1 mm Hg | Solubility in Water at 25° C. | Concentration of Saturated Headspace at 25° C. (M) |
|---|---|---|---|---|---|
| Benzaldehyde | Aldehyde | 180 | 26.2 | sl. soluble | $4.8 \times 10^{-5}$ |
| Salicylaldehyde | Aldehyde | 197 | 33.0 | sl. soluble | $3.6 \times 10^{-5}$ |
| Phenol | Alcohol | 182 | 40.1 | soluble | $2.1 \times 10^{-5}$ |
| Hydrocinnamaldehyde[a] | Aldehyde | 224 | — | sl. soluble | |
| Cuminaldehyde | Aldehyde | 236 | 58.0 | insoluble | $6.4 \times 10^{-6}$ |
| Thymol | Alcohol | 232 | 64.3 | sl. soluble | $2.9 \times 10^{-6}$ |
| Cinnamyl alcohol | Alcohol | 250 | 72.6 | soluble | $2.4 \times 10^{-6}$ |
| Cinnamaldehyde | Aldehyde | 251 | 76.1 | sl. soluble | $1.9 \times 10^{-6}$ |
| Methyl cinnamate | Ester | 262 | 77.4 | insoluble | $1.6 \times 10^{-6}$ |
| Eugenol | Alcohol | 254 | 78.4 | insoluble | $1.6 \times 10^{-6}$ |
| Isoeugenol | Alcohol | 268 | 86.3 | sl. soluble | $1.3 \times 10^{-6}$ |
| Ethyl cinnamate | Ester | 271 | 87.6 | insoluble | $7.0 \times 10^{-7}$ |
| Benzoic acid | Acid | 249 | 96.0 | soluble | $1.0 \times 10^{-7}$ |
| Vanillin | Aldehyde | 285 | 107.0 | sl. soluble | $1.0 \times 10^{-7}$ |

[a]Vapor pressure data on hydrocinnamaldehyde was not available.

All tubers weighed between 150–300 g and were free of any evident damage or disease. Substantially pure compounds were used as received from the manufacturers without further purification.

Six potato tubers were removed from cold storage and placed on ceramic platforms enclosed in 9.2 l dessicator flasks in a growth chamber at 25° C. Each flask contained either one 15-cm piece of Whatman No. 1 filter paper saturated with 1.0 ml if the compound was a liquid, or 1.0 g of powder if the compound was solid at 25° C. (control flasks lacked any compounds). These amounts were sufficient to theoretically produce a saturated headspace gas in the flasks. The compounds were placed at the bottom of the dessicator so that no direct physical contact with the tubers occurred. Tubers were then placed in the dark at 25° C. for 7 days, at which time all control tubers displayed sprouting. Tubers were visually rate for percentage of eyes sprouted, tuber appearance and texture, and presence of fungal growth. These conditions were selected to promote rapid sprouting of the controls to enable evaluation of all compounds within this relatively short time period, and to prevent variations in tuber age among treatments from affecting the results. All trials were conducted at the same environmental conditions, including temperature, to ensure consistent respiration conditions for all tubers between tests of different compounds. Each experiment was replicated once and the experiments were repeated once.

Because these compounds were difficult to quantitate by gas chromatography at the concentration levels in saturated headspaces, theoretical saturated concentrations were calculated by converting known vapor pressures of each compound at 25° C. to molar concentrations using the Ideal Gas Law, $n/V = P/RT$, where $n/V$ is the molar concentration, P is the partial pressure (atm), R is the Ideal Gas constant (0.0821 l atm/mol ° K.), and T is the temperature (° K.).

TABLE II

Sprout Inhibition, Fungal Growth, and Tuber Quality of Potato Tubers Exposed to Aromatic Compounds in Headspace Gas for 7 Days

| Treatment | % Eyes Sprouted | Fungal Growth[a] | Tuber Texture[b] |
|---|---|---|---|
| Control | 100 | ++ | SS |
| Benzoic acid | 98 | + | SS |
| Eugenol | 94 | ++ | F |
| Cinnamyl alcohol | 91 | + | SS |
| Isoeugenol | 89 | ++ | F |
| Vanillin | 87 | + | F |
| Ethyl cinnamate | 64 | + | F |
| Methyl cinnamate | 16 | − | F |
| Benzaldehyde | 0 | − | F |
| Cinnamaldehyde | 0 | − | F |
| Cuminaldehyde | 0 | − | F |
| Hydrocinnamaldehyde | 0 | − | F |
| Phenol | 0 | − | S,N |
| Salicylaldehyde | 0 | − | F |
| Thymol | 0 | − | F |
| LSD (0.05) | 12 | | |

[a]Visual ratings of fungal growth as follows: − = no fungi visible; + = some fungi; ++ = heavy fungal growth.
[b]Tuber texture ratings: F = firm; S = soft; SS = slightly soft; N = necrotic tissue.

The experimental results from tubers continuously exposed to saturated aromatic aldehyde or alcohol levels for 7 days are shown in Table II. After this period of time, control tubers had sprouted heavily, and most displayed heavy amounts of readily evident fungal mycelia. Benzaldehyde, cinnamaldehyde, cuminaldehyde, hydrocinnamaldehyde, salicylaldehyde, phenol and thymol completely inhibited sprouting and also prevented any visible fungal growth. All of the tubers in these treatments were firm and appeared healthy, except for the phenol treatment in which the tubers were blackened, soft to the touch, and displayed evident tissue necrosis. Benzoic acid, cinnamyl alcohol, eugenol and isoeugenol had no significant effect on tuber sprouting, while vanillin only slightly suppressed sprouting. Fungal growth was also present to some extent on all of these treatments, with especially heavy growth on the eugenol and isoeugenol treated tubers (although tubers that had received these treatments remained firm). It is of interest to note that benzoic acid and vanillin displayed little or no inhibition of sprouting even though both of these compounds have been reported to be allelopathic [Putnam and Tang, ibid.]. Control and benzoic acid treated tubers were soft to the touch, and the cinnamyl alcohol treated tubers were slightly soft. Ethyl and methyl cinnamate both suppressed sprouting to some degree and, in addition, methyl cinnamate suppressed fungal growth.

EXAMPLE 2

Tubers treated with several of the aromatic compounds did not being sprouting within a short time (4-7 days) after removal from the treatment flasks of Example 1. Therefore, compounds that completely inhibited sprouting without causing tuber damage were further examined as to the length of exposure to the volatilized compounds required for inhibition of sprouting for an extended time period after removal from treatment. Each treatment consisted of placing the tubers in sealed 9.2 l flasks containing excess levels of the treatment compounds at 25° C. as in Example 1. Three tubers were then removed from each treatment after 1, 2, 4, 7, and 10 days, and placed in flasks containing fresh humidified air (free of any additional volatilized compounds) at 25° C. Control tubers were placed in sealed flasks lacking any added compounds and three were removed after 1 and 10 days. Fourteen days after removal from the sealed flasks containing treatment compounds, all tubers were examined for percentage of eyes sprouted, tuber texture, and fungal growth. Each treatment was replicated once and each experiment was repeated once.

The results 14 days after removal of the tubers from exposure to saturated headspace gasses of benzaldehyde, cinnamaldehyde, cuminaldehyde, hydrocinnamaldehyde, salicylaldehyde and thymol are shown in Table III. After 14 days both groups of control tubers were heavily sprouted, were soft to the touch, and most possessed several patches of white, tufty fungal mycelia. Salicylaldehyde completely inhibited tuber sprouting after 1 or more days of treatment, and the tubers were firm and lacked visible fungal growth. Benzaldehyde, cinnamaldehyde, cuminaldehyde, and thymol exposure for 10 days completely inhibited sprouting, but exposure for 7 or fewer days by any of these compounds did not completely inhibit sprouting. All of these treatments were significantly inhibitory to fungal growth, although a small amount of mycelia was detected in a bruised area from a cinnamaldehyde-treated tuber. Treated tubers were generally quite firm, except those from 1 day benzaldehyde and thymol treatments, which were judged to be slightly soft. Tubers exposed to vapors of benzaldehyde, cinnamaldehyde, cuminaldehyde and salicylaldehyde for 10 days all remained unsprouted 75 days after the tubers were removed from treatment flasks. Most treated tubers also remained firm to the touch and lacked any visible rotting or fungal growth after this time period.

The observations hereinabove suggest that tubers may only need treatment for a reltaively short period of time and that continual application would not be necessary for long-term storage. Such short-term treatment would greatly lessen costs to the potato industry.

TABLE III

| Treatment | % Eyes Sprouted | Fungal Growth[a] | Tuber Texture[b] |
|---|---|---|---|
| Control | | | |
| 1 Day | 96 | + | SS |
| 10 Days | 100 | + | SS |
| Benzaldehyde | | | |
| 1 Day | 88 | − | SS |
| 2 Days | 42 | − | F |
| 4 Days | 14 | − | F |
| 7 Days | 2 | − | F |
| 10 Days | 0 | − | F |
| Cinnamaldehyde | | | |
| 1 Day | 62 | − | F |
| 2 Days | 80 | + | F |
| 4 Days | 64 | − | F |
| 7 Days | 24 | − | F |
| 10 Days | 0 | − | F |
| Cuminaldehyde | | | |
| 1 Day | 63 | − | F |
| 2 Days | 68 | − | F |
| 4 Days | 49 | − | F |
| 7 Days | 8 | − | F |
| 10 Days | 0 | − | F |
| Hydrocinnamaldehyde | | | |
| 1 Day | 90 | − | F |
| 2 Days | 79 | − | F |
| 4 Days | 66 | − | F |
| 7 Days | 51 | − | F |
| 10 Days | 24 | − | F |
| Salicylaldehyde | | | |
| 1 Day | 0 | − | F |
| 2 Days | 0 | − | F |
| 4 Days | 0 | − | F |
| 7 Days | 0 | − | F |
| 10 Days | 0 | − | F |
| Thymol | | | |
| 1 Day | 83 | + | SS |
| 2 Days | 60 | + | F |
| 4 Days | 44 | + | F |
| 7 Days | 6 | − | F |
| 10 Days | 0 | − | F |
| LSD (0.05) | 24 | | |

[a]Visual ratings of fungal growth: − = no fungi visible; + = some fungi visible.
[b]Tuber texture ratings: F = firm; SS = slightly soft.

EXAMPLE 3

Because the aromatic aldehydes and alcohols may be applied to the stored potatoes by methods other than as volatiles, direct application of the compounds either as pure chemicals or as emulsions was also studied. Emulsions were prepared as either 1% or 10% (v/v) of each compound in distilled water containing 0.05% (v/v) Tween 80 as an emulsifier (control tubers were treated with Tween 80 only). Tubers were treated by dipping each tuber in the test emulsion for 10 seconds, whereupon excess liquid was allowed to drain off. Pure compounds in liquid phase were applied with an atomizing sprayer, ensuring that the entire tuber surface was coated. Each tuber was sprayed with approximately 0.1-0.2 ml of each compound tested. Six tubers per treatment were used, with two replicates, and all experiments were repeated once. Tubers were then placed on ceramic platforms in dessicator flasks maintained at 25° C. and at 95% relative humidity for 14 days. Tubers were evaluated as in Example 1 for percentage of sprouted eyes, tuber texture and quality, and fungal growth.

Results 14 days after direct application of the compounds, either in pure form or as 1% or 10% emulsions, are shown in Table IV. All controls displayed heavy sprouting after 14 days. Only 1% cinnamaldehyde and 10% benzaldehyde emulsions completely inhibited sprouting without damaging the potato tubers. Tubers treated in this manner remained hard, with no necrosis or surface pitting, although the benzaldehyde-treated tubers were heavily covered with fungal growth. One percent thymol treatment suppressed sprouting but also gave rise to large pitted areas on the tuber surface near each eye, even though the pitted areas and the rest of the tuber surface remained firm to the touch. Application of the other treatment compounds, at the concentrations tested, caused some deleterious softening and necrosis.

TABLE IV

Tuber Sprouting, Texture, and Fungal Growth
14 Days After Direct Application of Aromatic Compounds

| Treatment | % Eyes Sprouted | Fungal Growth[a] | Tuber Texture[b] |
|---|---|---|---|
| Control | 98 | + | SS |
| Benzaldehyde | | | |
| 1% | 43 | + | F |
| 10% | 0 | ++ | F |
| 100% | 0 | ++ | S,N |
| Cinnamaldehyde | | | |
| 1% | 0 | − | F |
| 10% | 0 | + | S,N |
| 100% | 0 | − | S,N |
| Cuminaldehyde | | | |
| 1% | 5 | − | F |
| 10% | 43 | + | SS,N |
| 100% | 0 | − | SS,N |
| Eugenol | | | |
| 1% | 32 | ++ | SS |
| 10% | 7 | + | SS,N |
| 100% | 0 | − | S,N |
| Hydrocinnamaldehyde | | | |
| 1% | 25 | − | F |
| 10% | 0 | ++ | S |
| 100% | 0 | − | S,N |
| Salicylaldehyde | | | |
| 1% | 0 | ++ | S,N |
| 10% | 0 | − | S,N |
| 100% | 0 | − | S,N |
| Thymol | | | |
| 1% | 0 | − | F,P |
| 10% | 0 | − | SS,N,P |
| LSD (0.05) | 14 | | |

[a]Visual ratings of fungal growth: − = no fungi visible; + = some visible fungi; ++ = heavy fungal growth.
[b]Tuber texture ratings: F = firm; S = soft; SS = slightly soft; N = necrotic tissue; P = pitted tuber surfaces.

It is understood that the foregoing detailed description is given merely by way of illustration and that modifications and variations may be made therein without departing from the spirit and scope of the invention.

We claim:

1. A method for inhibiting sprouting of tubers comprising the step of exposing tubers to a sprout inhibiting effective amount of an aromatic aldehyde or alcohol selected from the group consisting of benzaldehyde, salicylaldehyde, cinnamaldehyde, hydrocinnamaldehyde, thymol, and mixtures thereof.

2. A method as described in claim 1 wherein said aromatic aldehyde is benzaldehyde.

3. A method as described in claim 2 wherein said benzaldehyde is substantially pure.

4. A method as described in claim 3 wherein said benzaldehyde is in a composition with a carrier.

5. A method as described in claim 1 wherein said aromatic aldehyde is salicylaldehyde.

6. A method as described in claim 5 wherein said salicylaldehyde is substantially pure.

7. A method as described in claim 6 wherein said salicylaldehyde is in a composition with a carrier.

8. A method as described in claim 1 wherein said aromatic aldehyde is cinnamaldehyde.

9. A method as described in claim 8 wherein said cinnamaldehyde is substantially pure.

10. A method as described in claim 9 wherein said cinnamaldehyde is in a composition with a carrier.

11. A method as described in claim 1 wherein said aromatic aldehyde is hydrocinnamaldehyde.

12. A method as described in claim 11 wherein said hydrocinnamaldehyde is substantially pure.

13. A method as described in claim 12 wherein said hydrocinnamaldehyde is in a composition with a carrier.

14. A method as described in claim 1 wherein said aromatic alcohol is thymol.

15. A method as described in claim 14 wherein said thymol is substantially pure.

16. A method as described in claim 15 wherein said hydrocinnamaldehyde is in a composition with a carrier.

17. A method as described in claim 1 wherein said aromatic aldehyde or alcohol is in a composition comprising an oleaginous fraction, and wherein said aromatic aldehyde or alcohol comprises more than 1% of said oleaginous fraction.

18. A method as described in claim 17 wherein said aromatic aldehyde or alcohol comprises more than 5% of said oleaginous fraction.

19. A method as described in claim 1, wherein said aromatic aldehyde or alcohol is a liquid and said step of exposing includes the step of allowing said liquid to volatilize into the atmosphere adjacent said tubers.

20. A method as described in claim 1, wherein said aromatic aldehyde or alcohol is a gas.

21. A method as described in claim 1, wherein said tubers are potatoes.

22. A method for inhibiting sprouting of tubers comprising the step of exposing tubers to a sprout inhibiting effective amount of a composition comprising an oleaginous fraction, and wherein said oleaginous fraction comprises more than 1% cuminaldehyde.

23. A method as described in claim 22 wherein said cuminaldehyde comprises more than 5% of said oleaginous fraction.

24. A method as described in claim 22 wherein said cuminaldehyde is substantially pure.

25. A method as described in claim 22, wherein said cuminaldehyde is a liquid and said step of exposing includes the step of allowing said liquid to volatilize into the atmosphere adjacent said tubers.

26. A method as described in claim 22, wherein said cuminaldehyde is a gas.

27. A method as described in claim 22, wherein said tubers are potatoes.

* * * * *